United States Patent [19]

Cevasco et al.

[11] Patent Number: 4,904,816

[45] Date of Patent: Feb. 27, 1990

[54] PROCESS FOR THE MANUFACTURE OF ANILINOFUMARATE VIA CHLOROMALEATE OR CHLOROFUMARATE OR MIXTURES THEREOF

[75] Inventors: Albert A. Cevasco; Donald Roy, both of Somerset, N.J.

[73] Assignee: American Cyanamid Company, Stamford, Conn.

[21] Appl. No.: 366,554

[22] Filed: Jun. 15, 1989

[51] Int. Cl.[4] ........................................... C07C 101/453
[52] U.S. Cl. ...................................... 560/44; 546/170
[58] Field of Search ........................... 560/44; 546/170

[56] References Cited

U.S. PATENT DOCUMENTS

| 4,656,283 | 4/1987 | Doehner | 560/44 |
| 4,675,432 | 6/1987 | Maulding et al. | 560/44 |
| 4,814,486 | 3/1989 | Maulding et al. | 560/44 |
| 4,843,162 | 6/1989 | Doehner | 560/44 |

FOREIGN PATENT DOCUMENTS 71545  3/1970  German Democratic Rep. ... 560/44

Primary Examiner—Bruce Gray
Attorney, Agent, or Firm—John W. Hogan, Jr.

[57] ABSTRACT

There is provided a novel process for the manufacture of anilinofumarate via chloromaleate or chlorofumarate or mixtures thereof.

8 Claims, No Drawings

PROCESS FOR THE MANUFACTURE OF ANILINOFUMARATE VIA CHLOROMALEATE OR CHLOROFUMARATE OR MIXTURES THEREOF

SUMMARY OF THE INVENTION

The invention herein described relates to a novel process for the preparation of anilinofumarate via chloromaleate or chlorofumarate or mixtures thereof. Anilinofumarate is an important intermediate in the preparation of a class of highly potent herbicidal agents, 2-(imidazolin-2-yl)quinoline-3-carboxylates.

It has now been found that anilinofumarates of formula I may be prepared efficiently and effectively from chloromaleates of formula II or chlorofumarates of formula III or mixtures thereof by reacting the chloromaleate or chlorofumarate with about 1.0 to 1.5 equivalents of aniline in the presence of about 1.0 to 1.8 molar equivalents of base as about a 15% to 50% aqueous solution containing phase transfer catalyst at an elevated temperature. The reaction is illustrated in Diagram I wherein R is $C_1$–$C_4$ alkyl.

DIAGRAM I

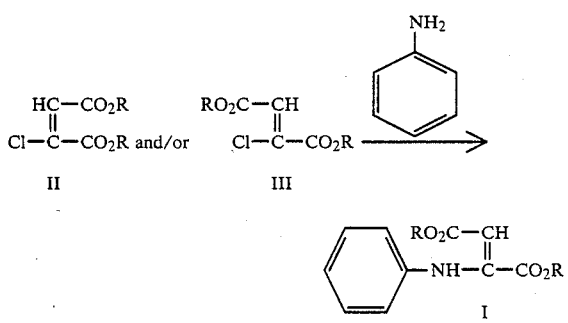

The thus-obtained anilinofumarates of formula I may be converted to quinoline-2,3-dicarboxylic acid (as shown in Diagram II), useful as an intermediate in the preparation of 2-(imidazolin-2-yl)quinoline-3-carboxylate herbicidal agents.

FLOW DIAGRAM II

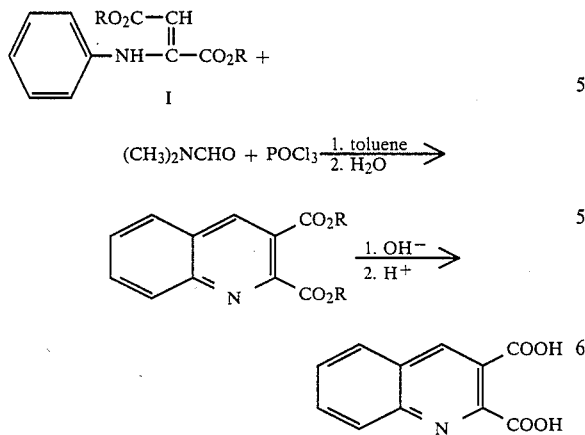

DESCRIPTION OF THE INVENTION

The present invention relates to a novel and efficient process for preparing anilinofumarates of formula I from chloromaleates of formula II or chlorofumarates of formula III, or mixtures thereof, as illustrated in diagram I, shown hereinabove, wherein R is $C_1$–$C_4$ alkyl. The anilinofumarates thus-produced are useful in the preparation of quinoline-2,3-dicarboxylic acid as shown hereinabove in flow diagram II. Quinolin-2,3-dicarboxylic acid is an important intermediate in the manufacture of 2-(imidazolin-2-yl)quinoline-3-carboxylates a class of potent herbicidal agents.

In accordance with the method of the present invention, anilinofumarates of formula I are prepared by reacting chloromaleates of formula II or chlorofumarates of formula III, or mixtures thereof, with about 1.0–1.5 molar equivalents of aniline in the presence of about 1.0–1.8 (preferably 1.0–1.5) molar equivalents of an aqueous base as about a 15% to 50% (preferably 20% to 30%) aqueous solution containing a phase transfer catalyst at an elevated temperature preferably about 70°–110° C., with 90°–95° C. being especially preferred. The reaction may optionally be conducted in the presence of an organic co-solvent which has a boiling point within 100° C. and 250° C. The product anilinofumarate is isolated using conventional isolation procedures such as extraction into an organic solvent followed by distillation.

Bases preferred for use in the present method are alkali metal bases, for example sodium and potassium hydroxides, bicarbonates or carbonates, especially preferred is sodium carbonate.

Preferred phase transfer catalysts employed in the present invention include tetraalkylated ammonium salts such as tetra-n-butylammonium bromide, tricaprylylmethylammonium chloride, tetrabutylammonium hydrogen sulfate, benzyltriethylammonium chloride, tributylmethylammonium chloride and the like.

In order to facilitate a further understanding of the invention, the following examples are presented primarily for the purpose of illustrating more specific details thereof. The invention is not be be limited thereby except as defined in the claims. Unless otherwise noted, all parts are by weight.

EXAMPLE 1

Preparation of diethyl anilinofumarate from diethyl chloromaleate

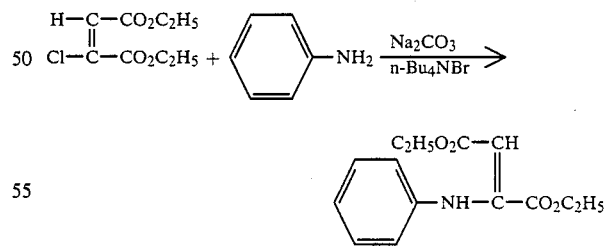

Tetra-n-butylammonium bromide (1.0 g, 0.003 mole) is added to a 23.5% aqueous solution of sodium carbonate (9.3 g, 0.088 mole). Chlorodiethylmaleate (13.7 g, 0.0663 mole) is added at 20°–25° C. followed by the addition of aniline (6.5 g, 0.070 mole). The reaction mixture is heated to 95° C. over 30 minutes and held at this temperature for 2 hours. Toluene (20.0 mL) is added to facilitate phase separation and the phases are separated at 40°–50° C. The organic product phase is washed with water (20 mL), and the anilinofumarate product is dried by azeotropic distillation, to give 17.54 g (86.6% pure by gas-liquid chromatography analysis, 87.0% yield).

EXAMPLE 2

Preparation of diethyl anilinofumarate from diethyl chlorofumarate

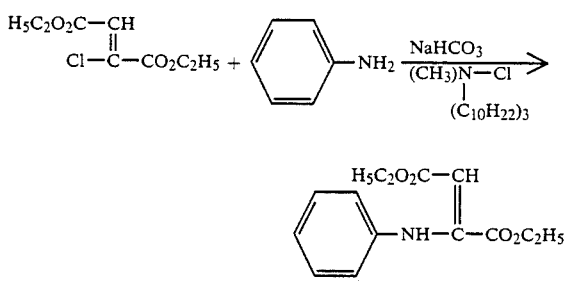

To a stirred solution of diethyl chlorofumarate (2.1 g, 0.01 mole) in toluene is added aniline (0.93 g, 0.01 mole), and 6.72 g of 15% aqueous sodium bicarbonate and tricaprylylmethyl ammonium chloride (0.20 g, 0.005 mole). The reaction mixture is heated at 75° C.–80° C. for 10 hours. Analysis of the organic phase by gas-liquid chromatography indicates a 71% yield of diethyl anilinofumarate.

EXAMPLE 3

Preparation of diethyl quinoline-2,3-dicarboxylate from anilinofumarate

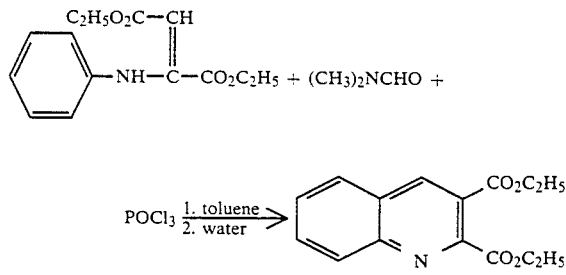

Phosphorus oxychloride (15.1 g, 9.0 mL, 0.098 mole) is added over a 20 minute period at 14°–23° C. to a solution of dimethylformamide (7.2 g, 0.098 mole) in toluene. The two phase reaction mixture is stirred for 1 hour at 23°–25° C., cooled to 16° C., and treated with a solution of anilinofumarate (21.92 g, 0.0833 mole) in toluene over a 30 minute period at 16°–22° C. The reaction mixture is stirred for 1 hour at 23° C., and heated to reflux temperature (110° C.) for about 2 hours. After cooling to 105° C., the reaction mixture is quenched with water. The organic layer is washed with 20 mL of water and concentrated in vacuo to give the title product, 30.0 g (63.5% pure by gas-liquid chromatography analysis, 83.7% yield).

EXAMPLE 4

Preparation of diethyl quinoline-2,3-dicarboxylic acid

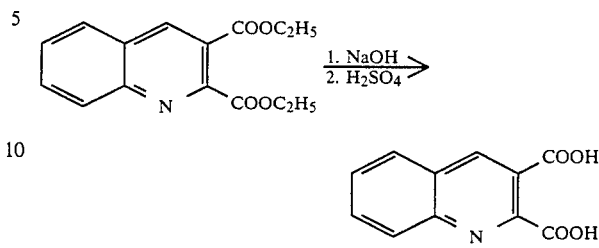

A solution of diethyl quinoline-2,3-dicarboxylate (15.60 g, 0.0567 mole) in toluene is added to a solution of 50% sodium hydroxide (16.7 g, 0.21 mole NaOH) in water and heated at reflux temperature, with stirring, for a 3 hour period. The toluene/water/ethanol azeotrope is removed by distillation. The remaining reaction mixture is cooled to room temperature and treated with a solution of sulfuric acid (12.8 g of 96% $H_2SO_4$, 0.125 mole) in water, with cooling to 30° C., to pH 1.4. After a 10 minute period at 30° C., the reaction mixture is filtered and the filter cake is washed with water and dried in vacuo to give the title product, 12.2 g, (97.4% pure by high pressure liquid chromatography analysis, 96.6% yield).

What is claimed is:

1. A method for the preparation of anilinofumarate of formula I

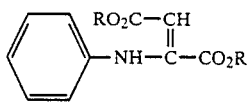

wherein R is $C_1$–$C_4$ alkyl which comprises reacting chloromaleate of formula II or chlorofumarate of formula III or mixtures thereof

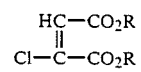

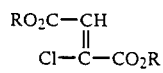

wherein R is $C_1$–$C_4$ alkyl with about 1.0 to 1.5 molar equivalents of aniline in the presence of about 1.0 to 1.8 molar equivalents of aqueous base containing a phase transfer catalyst to form the anilinofumarate.

2. A method according to claim 1 wherein the aqueous base is a 15% to 50% aqueous solution of an alkali metal hydroxide, bicarbonate or carbonate.

3. A method according to claim 2 wherein the base is sodium carbonate present as about a 20% to 30% aqueous solution.

4. A method according to claim 1 wherein the phase transfer catalyst is a tetraalkylated ammonium salt.

5. A method according to claim 4 wherein the phase transfer catalyst is tetra-n-butylammonium bromide.

6. A method according to claim 1 wherein the method is carried out at a temperature of about 70° C. to 110° C.

7. A method according to claim 6 wherein the temperature is about 90° C. to 95° C.

8. A method according to claim 1 wherein the Formula II chloromaleate is diethyl chloromaleate.

* * * * *

UNITED STATES PATENT OFFICE
CERTIFICATE OF CORRECTION

Patent No. 4,904,816  Dated February 27, 1990

Inventor(s) Albert Anthony Cevasco et al.

It is certified that error appears in the above-identified patent and that said Letters Patent is hereby corrected as shown below:

On the cover page, the left column, the lines under item No. 75 should read:

--Albert A. Cevasco, Belle Mead; Donald Roy Maulding, Somerville, both of New Jersey--

Signed and Sealed this

Second Day of March, 1993

*Attest:*

STEPHEN G. KUNIN

*Attesting Officer*   Acting Commissioner of Patents and Trademarks